United States Patent [19]

Narayanan

[11] Patent Number: 5,338,762
[45] Date of Patent: Aug. 16, 1994

[54] WATER-BASED MICROEMULSUION FORMULATION OF A CARBAMATE ESTER

[75] Inventor: Kolazi S. Narayanan, Palisades Park, N.J.

[73] Assignee: ISP Investments Inc., Wilmington, Del.

[21] Appl. No.: 978,860

[22] Filed: Nov. 19, 1992

Related U.S. Application Data

[63] Continuation-in-part of Ser. No. 777,033, Oct. 16, 1991, abandoned, which is a continuation-in-part of Ser. No. 654,250, Feb. 12, 1991, abandoned, which is a continuation-in-part of Ser. No. 546,014, Jun. 28, 1990, Pat. No. 5,156,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^5$ .............. A01N 25/00; A01N 37/18
[52] U.S. Cl. .................... 514/788; 514/613; 514/615
[58] Field of Search ............. 71/93, 87, 88, 96, 116, 71/117, 118, DIG. 1; 514/970, 937, 938, 942, 788, 613, 615

[56] References Cited

FOREIGN PATENT DOCUMENTS 6985393  8/1968  South Africa .

OTHER PUBLICATIONS

Chemical Abstracts (109:131269m) 1988.

Primary Examiner—Marianne M. Cintins
Assistant Examiner—K. Weddington
Attorney, Agent, or Firm—Walter Katz; Marilyn J. Maue; Joshua J. Ward

[57] ABSTRACT

A clear, efficacious, aqueous microemulsion of an agriculturally active carbamate ester insecticide.

5 Claims, No Drawings

WATER-BASED MICROEMULSUION FORMULATION OF A CARBAMATE ESTER

CROSS-REFERENCE TO RELATED APPLICATIONS

This application is a continuation-in-part of application Ser. No. 777,033, filed Oct. 16, 1991, now abandoned which is a continuation-in-part of application Ser. No. 654,250, filed Feb. 12, 1991, now abandoned which, in turn, is a continuation-in-part of application Ser. No. 546,014, filed Jun. 28, 1990, now U.S. Pat. No. 5,156,666 which, in turn, is a continuation-in-part of application Ser. No. 505,030, filed Apr. 5, 1990, now U.S. Pat. No. 5,160,528 which, in turn, is a continuation-in-part of application Ser. No. 448,707, filed Dec. 11, 1989, now U.S. Pat. No. 5,071,463.

BACKGROUND OF THE INVENTION

1. Field of the Invention

This invention relates to a delivery system for agriculturally active chemicals, and, more particularly, to a clear, efficacious, aqueous microemulsion for delivering a carbamate ester at a high loading.

2. Description of the Prior Art

Agriculturally active chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants.

It is also desired to provide an aqueous microemulsion a carbamate ester which is stable upon formation, and which can be used within a relatively short time, e.g. 11 days, without significant hydrolysis or precipitation.

Accordingly, it is an object of the present invention to provide a clear, efficacious aqueous microemulsion of a carbamate ester which can be used without hydrolysis or crystal precipitation soon after formation.

SUMMARY OF THE INVENTION

What is provided herein is a clear, efficacious aqueous microemulsion of an agriculturally active insecticide which is a carbamate ester, which comprises:

(a) about 0.005–1% by weight of said carbamate ester, preferably 0.1–0.5%, (b) about 0.01–10% by weight of sodium dodecyl sulfate, (c) about 1–15% by weight of a $C_6$–$C_{18}$ alkyl pyrrolidone, preferably N-octylpyrrolidone, and (d) at least about 80% by weight of water, preferably 92–99.98%.

When the composition of the invention is buffered to a pH of about 6 with conventional inorganic acid buffers, such as $KH_2PO_4$, the formulation is stable towards hydrolysis. However, if both chemical and phase stability is desired, the formulation should be used soon after preparation because crystals of the active insecticide will precipitate after about 10 days.

DETAILED DESCRIPTION OF THE INVENTION

Carbaryl is a widely-used insecticide of the carbamate ester-type which chemically is 1-naphthyl-N-methyl carbamate. In accordance with the invention, a clear, efficacious aqueous, microemulsion of carbaryl was formulated having the following components, in parts by weight.

TABLE I

AQUEOUS MICROEMULSION COMPOSITION OF THE INVENTION

| Component | Amounts (% by Wt.) Suitable | Preferred |
| --- | --- | --- |
| (a) Carbaryl | 0.005–1 | 0.3 |
| (b) Anionic Surfactant, e.g. sodium dodecyl sulfonate | 0.01–10 | 2 |
| (c) $C_6$–$C_{18}$ alkyl pyrrolidone, e.g. octylpyrrolidone | 1–15 | 5 |
| (d) Water | >80 | 92.7 |
|  | 100.0 | 100.0 |

This composition is a stable, one-phase, efficacious microemulsion of pH 9.3 at ambient temperatures which is designed for use soon after preparation. However, chemical stability can be enhanced by buffering the formulation to a ph of about 6 with a suitable buffering agent, such as an inorganic acid, e.g. $KH_2PO_4$. This buffering agent, however, does not prevent precipitation of the active ingredient after 10 days, and, accordingly, the composition should be used within this period.

EXAMPLES

TABLE II

| | Run A | Run B | Run C | Run D* |
| --- | --- | --- | --- | --- |
| Microemulsion | | | | |
| Carbaryl | 0.1 | 0.5 | 0.3 | 0.3 |
| N-Octylpyrrolidone | 5 | 5 | 5 | 0.5 |
| Sodium Dodecyl Sulfate** | 2 | 2 | 2 | 2 |
| Water | 92.9 | 92.5 | 92.7 | 92.7 |
| Physical Stability: Time, observation at ambient conditions | | | | |
| 0 time | clear | clear | clear | clear |

TABLE II-continued

| | Run | | | |
|---|---|---|---|---|
| | A | B | C | D* |
| 1 day | clear | ppt | clear | clear |
| 2 days | clear | ppt | clear | clear |
| 4 days | clear | ppt | clear | clear |
| 6 days | clear & colorless | | clear | clear |
| 2 weeks | clear & colorless | clear-colorless | | clear |
| pH at 0 time | 8.0 | 8.0 | 8.4–9.3 | 6.0 |

*buffered with 5 ml of a 0.2M KH$_2$PO$_4$ solution for 95 g of the formulation
**from a 29% aqueous solution

RESULTS

The buffered formulation D above did not show any decay in the UV absorbance peak of λ max=279 nm of the active material in a period of 30 days at ambient temperature indicating chemical stability, i.e. little hydrolysis. However, tiny needle crystals of 50 microns in length of carbaryl started separating after 11 days.

While the invention has been described with particular reference to certain embodiments thereof, it will be understood that changes and modifications may be made which are within the skill of the art. Accordingly, it is intended to be bound only by the following claims, in which:

What is claimed is:

1. A clear, efficacious aqueous microemulsion of a carbamate ester comprising:
   (a) about 0.005–1% by weight of an agriculturally active carbamate ester,
   (b) about 0.01–10% by weight of sodium dodecyl sulfate,
   (c) about 1–15% by weight of a $C_6$–$C_{18}$ alkyl pyrrolidone, and
   (d) at least about 80% by weight of water.

2. A microemulsion according to claim 1 wherein said carbamate ester is 1-naphthyl-N-methyl carbamate.

3. A microemulsion according to claim 1 wherein (a) is 0.1–0.5%, (b) is 1–5%, (c) is 3–10%, and (d) is 84.5–95.9%.

4. A microemulsion according to claim 1 which is buffered to a pH of about 6.

5. A microemulsion according to claim 1 wherein (c) is N-octylpyrrolidone.

* * * * *